(12) United States Patent
Thai

(10) Patent No.: US 9,949,805 B1
(45) Date of Patent: Apr. 24, 2018

(54) ORTHODONTIC BRACE BRACKET ATTACHMENT SYSTEM

(71) Applicant: Hung M. Thai, San Jose, CA (US)

(72) Inventor: Hung M. Thai, San Jose, CA (US)

(*) Notice: Subject to any disclaimer, the term of this patent is extended or adjusted under 35 U.S.C. 154(b) by 285 days.

(21) Appl. No.: 14/717,522

(22) Filed: May 20, 2015

Related U.S. Application Data

(63) Continuation-in-part of application No. 14/167,098, filed on Jan. 29, 2014.

(51) Int. Cl.
*A61C 3/00* (2006.01)
*A61C 7/16* (2006.01)

(52) U.S. Cl.
CPC .................................. *A61C 7/16* (2013.01)

(58) Field of Classification Search
CPC .............. A61C 7/16; A61C 7/12; A61C 7/146
USPC ....................................................... 433/8–12
See application file for complete search history.

(56) References Cited

U.S. PATENT DOCUMENTS

| | | | |
|---|---|---|---|
| 3,932,940 A * | 1/1976 | Andren | A61C 7/12 433/9 |
| 4,094,068 A | 6/1978 | Schinhammer | |
| 4,604,057 A | 8/1986 | Viglietti | |
| 4,759,714 A * | 7/1988 | Szegvary | A61C 13/30 433/221 |
| 4,842,513 A | 6/1989 | Haarmann | |
| 4,936,773 A * | 6/1990 | Kawaguchi | A61C 7/12 433/8 |
| 5,902,104 A | 5/1999 | Yamada | |
| 2008/0085486 A1 | 4/2008 | Busch | |
| 2011/0047799 A1 | 3/2011 | Abels et al. | |
| 2011/0281228 A1 * | 11/2011 | Hirsch | A61C 7/14 433/8 |

* cited by examiner

*Primary Examiner* — Yogesh Patel

(57) ABSTRACT

An orthodontic bracket attachment system featuring brackets for orthodontic braces. The system features a wing located on a bracket facial side. The system features an adhesive indention located on a bracket lingual side. The orthodontic bracket is designed to be affixed to a surface of a tooth. Adhesive is applied to the bracket lingual side flowing into the adhesive indention. The bracket is affixed to the surface of the tooth via the adhesive.

17 Claims, 6 Drawing Sheets

ORTHODONTIC BRACE BRACKET ATTACHMENT SYSTEM

CROSS REFERENCE

This application claims priority to U.S. patent application Ser. No. 14/167,098, filed Jan. 29, 2014, the specification(s) of which is/are incorporated herein in their entirety by reference.

FIELD OF THE INVENTION

The present invention relates to brackets for orthodontic braces.

BACKGROUND OF THE INVENTION

Orthodontic brackets are a component in an orthodontic brace system that cements to a tooth of a wearer. On occasion, however, the orthodontic bracket can pop off of the tooth, requiring a trip to the orthodontist for reattachment, thus a need exists for an improved orthodontic bracket attachment system. The present invention features an orthodontic bracket attachment system.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

SUMMARY OF THE INVENTION

The present invention features an orthodontic bracket attachment system. In some embodiments, the system comprises an orthodontic bracket. In some embodiments, the system comprises a wing located on a bracket facial side. In some embodiments, the system comprises an adhesive indention located on a bracket lingual side.

In some embodiments, the orthodontic bracket is designed to be affixed to a surface of a tooth. In some embodiments, adhesive is applied to the bracket lingual side flowing into the adhesive indention. In some embodiments, the bracket is affixed to the surface of the tooth via the adhesive.

DESCRIPTION OF PREFERRED EMBODIMENTS

Figure 1:
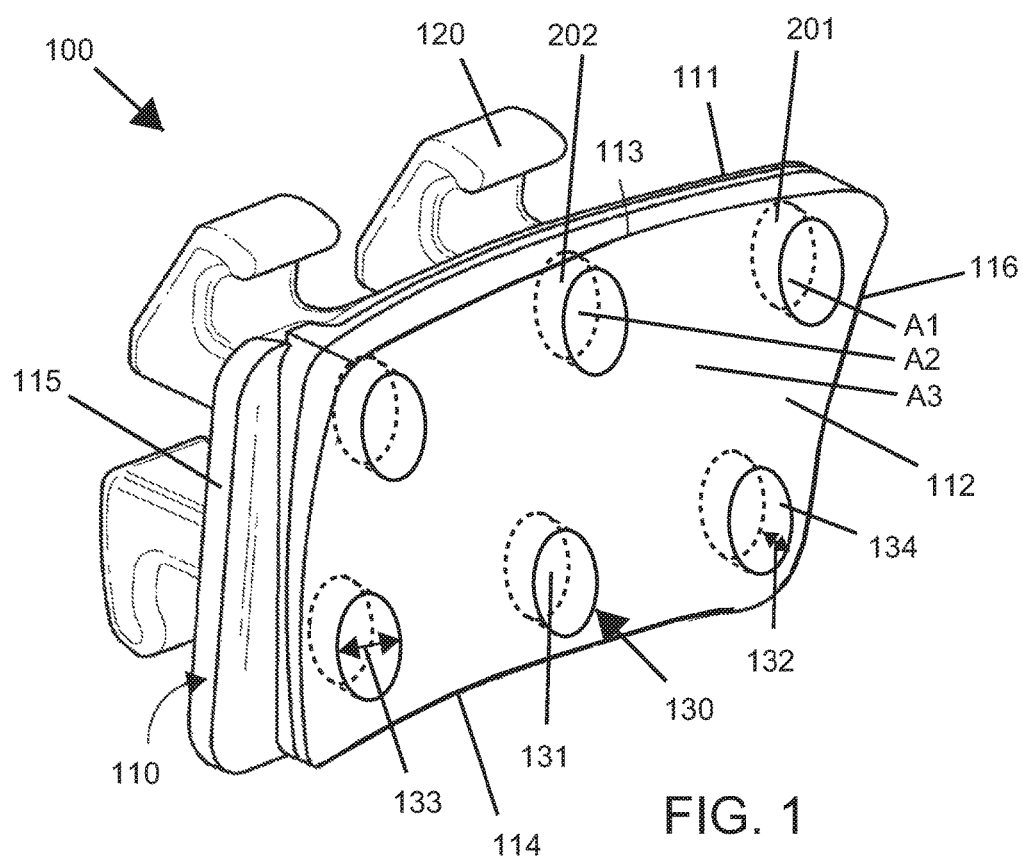
FIG. 1 shows a perspective view of the bracket lingual side of the present invention.

Following is a list of elements corresponding to a particular element referred to herein:
   100 Orthodontic bracket attachment system
   110 Bracket base
   111 Bracket facial side
   112 Bracket lingual side
   113 Bracket top
   114 Bracket bottom
   115 Bracket mesial side
   116 Bracket distal side
   120 Wing
   130 Adhesive indention
   131 Indention floor
   132 Indention depth
   133 Indention diameter
   134 Indention wall
   140 Pinhole channel Referring now to FIG. 1-5B, the present invention features an orthodontic bracket attachment system (100). In some embodiments, the system (100) comprises a bracket base (110) having a bracket facial side (111), a bracket lingual side (112), a bracket top (113), a bracket bottom (114), a bracket mesial side (115), and a bracket distal side (116).

Referring now to FIG. 1, the present invention features a wing (120) disposed on the bracket facial side (111). Orthodontic brackets (110) and wings (120) for wire attachment are well known to those of ordinary skill in the art.

In some embodiments, the system (100) comprises at least two separate and discrete adhesive indentions (130) disposed on the bracket lingual side (112). The adhesive indentions are definite undercut. In some embodiments, the indentions may be of any appropriate shape, for example, linear slots, square, oval and/or circular. See for example, FIG. 5.

In some embodiments, the first adhesive indention is located near a first side edge of the bracket base, and the second adhesive indention is located on the opposing second side edge of the bracket base, the first and second adhesive indention being elongated shape. See for example, FIG. 5D-5I.

In some embodiments, the adhesive indentions (130) comprise indention floors (131) offset from the bracket lingual side (112). As shown in FIG. 1 of the present invention, the bottom floors (131) of the adhesive indentions (130) are not directly interconnected to each other. The separate and discrete adhesive indentions (130) and detached indention floors (131) are beneficial for bracket attachment to the surface of the tooth since the peeling off of one adhesive indention can not affect the entire surface area of the lingual side (112) of the bracket base (110) when adhesive is applied to the bracket lingual side (112) flowing into adhesive indentions. This feature of having multiple discrete indentations where the respective bottom floors do not interconnect is uniquely different over Busch prior art (US 2008/0085486 A1). As shown in FIG. 4 in Busch patent application publication (US 2008/0085486 A1), the grooves (207) which are disposed on the top side, bottom side, mesial side and distal side of the etched bracket are interconnected with each other and spread all around the inner surface of the bracket lingual side. As a result, when adhesive is applied, the adhesive also fills in the entire grooves surface (207) of the tooth facing side of the bracket. The disadvantage of the interconnected groove floors of Busch patent application publication (US 2008/0085486 A1) is that the peeling off of partial anchoring surface area of the tooth facing side of the bracket will affect the entire surface area since adhesive is dispersed all over the entire interconnected groove surface of the bracket lingual side.

Figure 2:
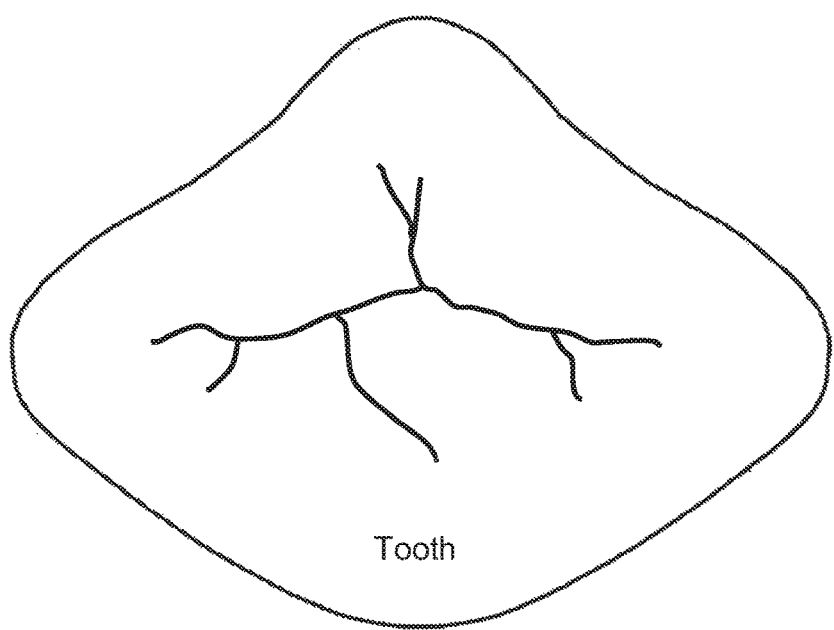
FIG. 2 shows a top view of the present invention.
Figure 2:
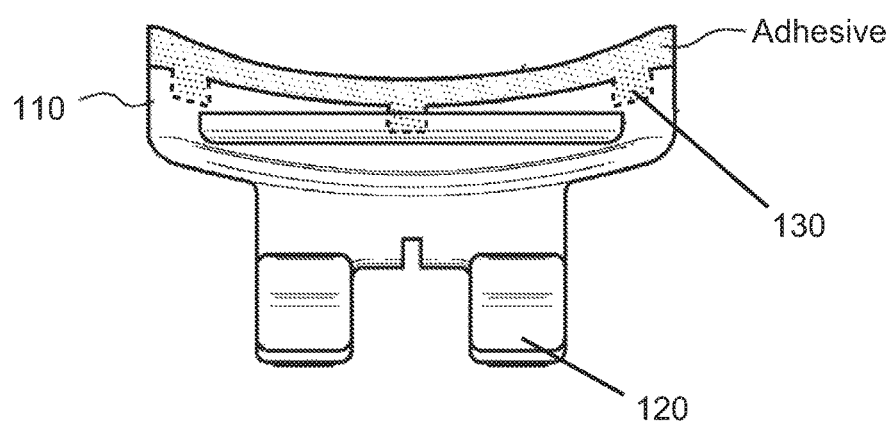
Figure 3:
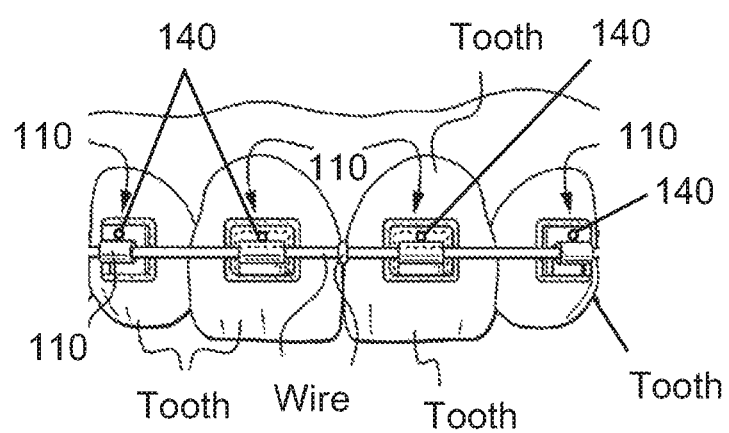
FIG. 3 shows a facial view of the present invention.
Figure 4A:
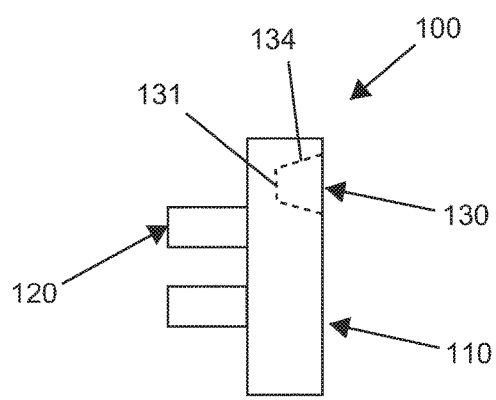
FIG. 4A shows a side view of an alternate embodiment of bracket of the present invention featuring the adhesive indention.
Figure 4B:
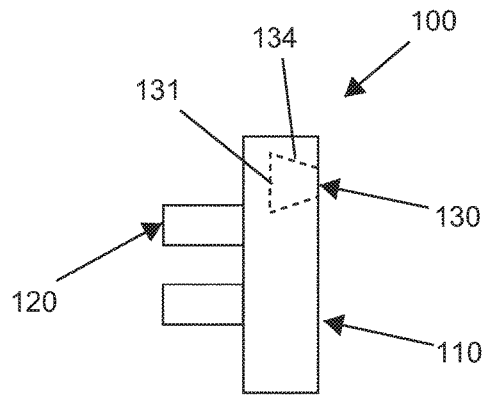
FIG. 4B shows a side view of an alternate embodiment of bracket of the present invention featuring the adhesive indention.
Figure 4C:
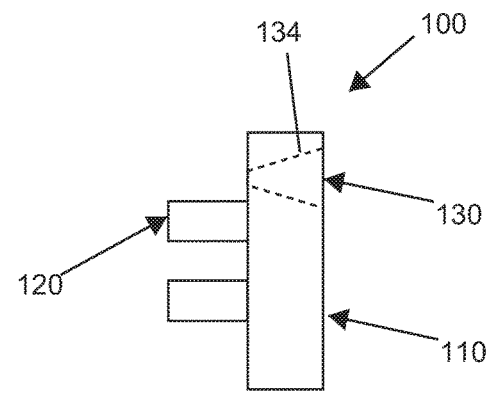
FIG. 4C shows a side view of an alternate embodiment of bracket of the present invention featuring the adhesive indention.
Figure 4D:
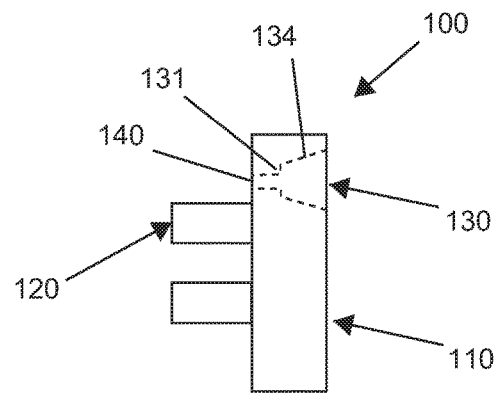
FIG. 4D shows a side view of an alternate embodiment of bracket of the present invention featuring the adhesive indention.
Figure 4E:
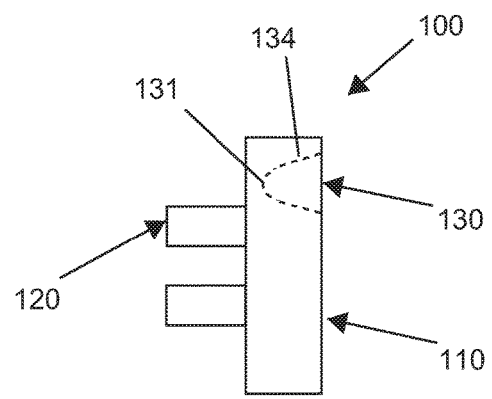
FIG. 4E shows a side view of an alternate embodiment of bracket of the present invention featuring the adhesive indention.
Figure 4F:
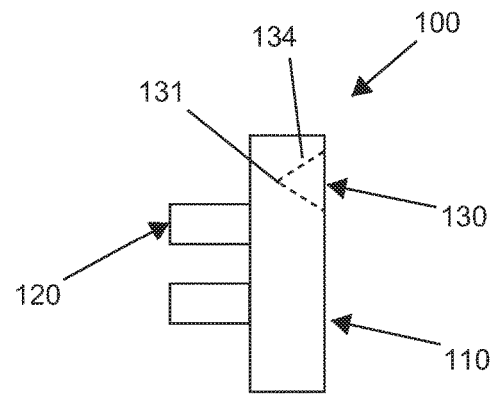
FIG. 4F shows a side view of an alternate embodiment of bracket of the present invention featuring the adhesive indention.
Figure 4G:
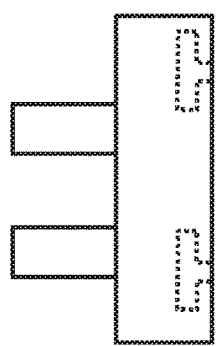
FIG. 4G shows a side view of an alternate embodiment of bracket of the present invention featuring the adhesive indention.
Figure 4H:
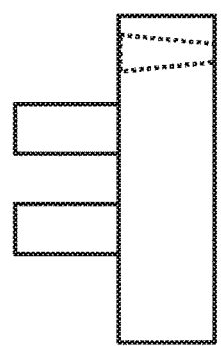
FIG. 4H shows a side view of an alternate embodiment of bracket of the present invention featuring the adhesive indention.
Figure 5A:
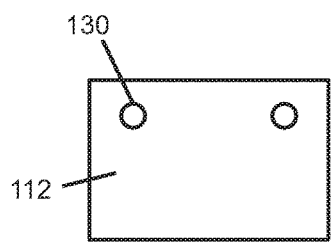
FIG. 5A-5I shows a lingual view of an alternate embodiment of bracket of the present invention featuring the adhesive indention.
Figure 5B:
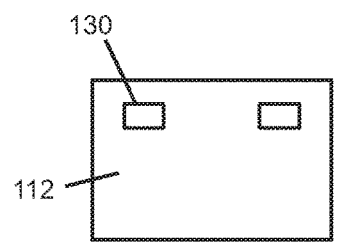
Figure 5C:
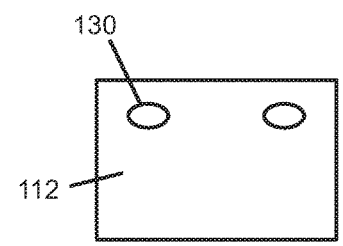
Figure 5D:
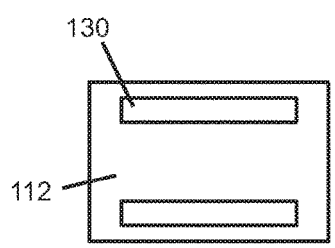
Figure 5E:
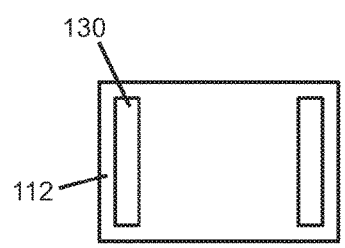
Figure 5F:
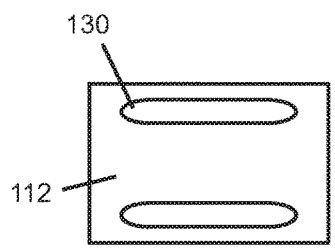
Figure 5G:
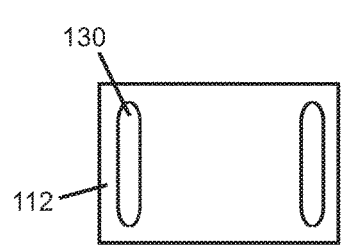
Figure 5H:
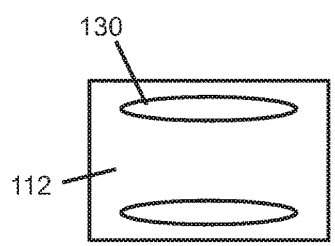
Figure 5I:
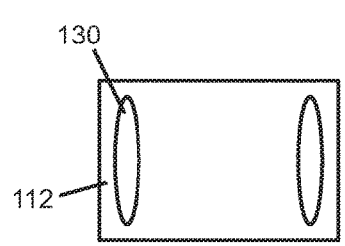

In some embodiments, the bottom floor of the first adhesive indention (201) has a first area unit (A1) and the bottom floor of the second adhesive indention (202) has a second area unit (A2). In some embodiments, the ratio of the sum of first and second adhesive indention area units (A1+A2) to the top surface area (A3) of the lingual side (112) is less than 1:8. This low area ratio of bottom floors (A1+A2, etc.) to the top surface area A3 is advantageous for bracket attachment to the surface of the tooth because the peeling off of one adhesive indention can not affect the anchoring surface of another adhesive indention as well as the anchoring surface of entire surface area of the lingual side (112) of the bracket base (110) when adhesive is applied to the bracket lingual side (112) flowing into adhesive indentions. In contrast, when the area ratio of the bottom floors of the adhesive indentions to the top surface area of the lingual side approaches 1:1, the whole anchoring surface of the grooves (207) which is adhered to the tooth surface bears a resemblance to a 'grid' as shown in FIG. 2 and FIG. 4 of Busch patent application publication (US 2008/0085486 A1). The particular disadvantage of this 'grid' like anchoring surface is that the adhesive is dispersed on entire interconnected grooves and peeling off of partial surface area will affect the entire surface area of the bracket lingual side.

In some embodiments, the bracket base (110) is designed to be affixed to a surface of a tooth. In some embodiments, adhesive is applied to the bracket lingual side (112) flowing into the adhesive indention (130). In some embodiments, the bracket is affixed to the surface of the tooth via the adhesive. Adhesives used for bracket base (110) attachment are well known to those of ordinary skill in the art.

In some embodiments, a plurality of adhesive indentions (130) is located on the bracket lingual side (112). In some embodiments, two adhesive indentions (130) are located on the bracket lingual side (112). In some embodiments, three adhesive indentions (130) are located on the bracket lingual side (112). In some embodiments, four or more adhesive indentions (130) are located on the bracket lingual side (112).

In some embodiments, the adhesive indention (130) comprises an indention floor (131). In some embodiments, the adhesive indention (130) comprises an indention depth (132) from the bracket lingual side (112) to the indention floor (131).

In some embodiments, the indention floor (131) is flat. In some embodiments, the indention floor (131) is hemispherical. In some embodiments, the indention floor (131) tapers to a point.

In some embodiments, the adhesive indention (130) comprises tapered indention walls (134) from the bracket lingual side (112) to the indention floor (131). In some embodiments, an indention diameter (133) decreases from the bracket lingual side (112) to the indention floor (131). In some embodiments, the adhesive indention (130) comprises tapered indention walls (134) from the bracket lingual side (112) to the indention floor (131). In some embodiments, an indention diameter (133) increases from the bracket lingual side (112) to the indention floor (131).

In some embodiments, the adhesive indention (130) is a channel located from the bracket facial side (111) to the bracket lingual side (112). In some embodiments, the channel passes entirely through the bracket base (110).

In some embodiments, the adhesive indention (130) is located proximal to the bracket top (113). In some embodiments, the adhesive indention (130) is located proximal to the bracket bottom (114). In some embodiments, the adhesive indention (130) is located proximal to the bracket mesial side (115) or the bracket distal side (116).

In some embodiments, the adhesive indention (130) is round at the bracket lingual side (112). In some embodiments, the adhesive indention (130) is rectangular at the bracket lingual side (112). In some embodiments, the adhesive indentation is polygonal at the bracket lingual side (112). In some embodiments, the adhesive indentation is irregularly shaped at the bracket lingual side (112).

In some embodiments, the indention floor (131) comprises a pinhole channel (140) located between the indention floor (131) and the bracket facial side (111). In some embodiments, the pinhole channel (140) is an air vent when adhesive is applied to the bracket lingual side (112) flowing into the adhesive indention (130).

As used herein, the term "about" refers to plus or minus 10% of the referenced number.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. Reference numbers recited in the claims are exemplary and for ease of review by the patent office only, and are not limiting in any way. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

The reference numbers recited in the below claims are solely for ease of examination of this patent application, and are exemplary, and are not intended in any way to limit the

What is claimed is:

1. An orthodontic bracket attachment system (100), wherein the system (100) comprises:
   (a) a bracket base (110) having a bracket facial side (111), a bracket lingual side (112), a bracket top (113), a bracket bottom (114), a bracket mesial side (115), and a bracket distal side (116);
   (b) a wing (120) disposed on the bracket facial side (111); and
   (c) at least two separate and discrete indentions (130) disposed on the bracket lingual side (112), wherein the indentions (130) are configured to receive adhesive;
wherein the indentions (130) comprise an indention floor (131) offset from the bracket lingual side (112), wherein a bottom floor (131) of a first indention (130) is not directly interconnected to the bottom floor of a second indention, wherein the bottom floor of the first indention (201) has a first area unit (A1) and the bottom floor of the second indention (202) has a second area unit (A2), wherein a ratio of the sum of first and second indention area units (A1+A2) to a top surface area (A3) of the lingual side (112) is less than 1:8,
wherein each indentation has an indentation diameter (133), wherein the indentations are spaced from each other such that a shortest distance between the indentations is at least equal to or greater than a maximum value of the indentation diameter (133) at the bracket lingual side (112).

2. The system (100) of claim 1, wherein the indention (130) comprises an indention depth (132) from the bracket lingual side (112) to the indention floor (131), wherein the indention floor (131) comprises a pinhole channel (140) disposed between the indention floor (131) and the bracket facial side (111); wherein each indention (130) comprises a single indention floor (131) within said indention (130), and a single pinhole channel (140) within said indention floor (131);
   wherein the bracket base (110) is designed to be affixed to a surface of a tooth, wherein adhesive is applied to the bracket lingual side (112) flowing into the discrete and separate indentions (130), wherein the pinhole channel (140) is an air vent such that adhesive applied to the bracket lingual side (112) flows into the discrete and separate indentions (130), allowing air to escape the indentions (130) through the pinhole channel (140), wherein the bracket is configured to affixed to the surface of the tooth via the adhesive.

3. The system (100) of claim 1, wherein a plurality of indentions (130) is disposed on the bracket lingual side (112).

4. The system (100) of claim 1, wherein the indention floor (131) is flat.

5. The system (100) of claim 1, wherein the indention floor (131) is hemispherical.

6. The system (100) of claim 1, wherein the indention floor (131) tapers to a point.

7. The system (100) of claim 1, wherein the indention (130) comprises tapered indention walls (134) from the bracket lingual side (112) to the indention floor (131), wherein the indention diameter (133) decreases from the bracket lingual side (112) to the indention floor (131).

8. The system (100) of claim 1, wherein the indention (130) comprises tapered indention walls (134) from the bracket lingual side (112) to the indention floor (131), wherein an indention diameter (133) increases from the bracket lingual side (112) to the indention floor (131).

9. The system (100) of claim 1, wherein the indentions (130) are disposed proximal to the bracket top (113).

10. The system (100) of claim 1, wherein the indentions (130) are disposed proximal to the bracket bottom (114).

11. The system (100) of claim 1, wherein the indentions (130) are disposed proximal to the bracket mesial side (115) or the bracket distal side (116).

12. The system (100) of claim 1, wherein the indentions (130) are round at the bracket lingual side (112).

13. The system (100) of claim 1, wherein the indentions (130) are rectangular at the bracket lingual side (112).

14. The system (100) of claim 1, wherein the indentations (130) are polygonal at the bracket lingual side (112).

15. An orthodontic bracket attachment system (100), wherein the system (100) comprises:
   (a) a bracket base (110) having a bracket facial side (111), a bracket lingual side (112), a bracket top (113), a bracket bottom (114), a bracket mesial side (115), and a bracket distal side (116);
   (b) a wing (120) disposed on the bracket facial side (111); and
   (c) at least two separate and discrete indentions (130) disposed on the bracket lingual side (112), wherein the indentions (130) are configured to receive adhesive;
wherein the indentions (130) comprise an indention floor (131) offset from the bracket lingual side (112), wherein a bottom floor (131) of a first indention (130) is not directly interconnected to the bottom floor of a second indention, wherein the bottom floor of the first indention (201) has a first area unit (A1) and the bottom floor of the second indention (202) has a second area unit (A2), wherein a ratio of the sum of first and second indention area units (A1+A2) to a top surface area (A3) of the lingual side (112) is less than 1:8;
wherein the first indention is located near a first side edge of the bracket base, and the second indention is located on the opposing second side edge of the bracket base,
wherein the indentations are spaced from each other such that a shortest distance between the indentations is at least equal to or greater than a maximum value of an indentation diameter (133) of each indentation, said indentation diameter (133) being measured at the bracket lingual side (112).

16. An orthodontic bracket attachment system (100), wherein the system (100) comprises:
   (a) a bracket base (110) having a bracket facial side (111), a bracket lingual side (112), a bracket top (113), a bracket bottom (114), a bracket mesial side (115), and a bracket distal side (116);
   (b) a wing (120) disposed on the bracket facial side (111); and
   (c) at least two separate and discrete indentions (130) disposed on the bracket lingual side (112), wherein the indentions (130) are configured to receive adhesive;
wherein the indentions (130) comprise an indention floor (131) offset from the bracket lingual side (112), wherein a bottom floor (131) of a first indention (130) is not directly interconnected to the bottom floor of a second indention, wherein the bottom floor of the first indention (201) has a first area unit (A1) and the bottom floor of the second indention (202) has a second area unit (A2), wherein a ratio of the sum of first and second indention area units (A1+A2) to a top surface area (A3) of the lingual side (112) is less than 1:8,
wherein the indention floor (131) comprises a pinhole channel (140) disposed between the indention floor (131) and the bracket facial side (111); wherein each indention (130)

comprises a single indention floor (131) within said indention (130), and a single pinhole channel (140) within said indention floor (131);

wherein a diameter of the pinhole channel at the bracket facial side (111) is smaller than an indentation diameter (133) of the indentation (130) at the bracket lingual side (112);

wherein the bracket base (110) is designed to be affixed to a surface of a tooth, wherein adhesive is applied to the bracket lingual side (112) flowing into the discrete and separate indentions (130), wherein the pinhole channel (140) is an air vent such that adhesive applied to the bracket lingual side (112) flows into the discrete and separate indentions (130), allowing air to escape the indentions (130) through the pinhole channel (140), wherein the bracket is configured to affixed to the surface of the tooth via the adhesive.

17. The system (100) of claim 16, wherein the indentations (130) are spaced from each other such that a shortest distance between the indentations is at least equal to or greater than a maximum value of the indentation diameter (133) at the bracket lingual side (112).

\* \* \* \* \*